(12) United States Patent
Fukuda

(10) Patent No.: US 8,863,583 B2
(45) Date of Patent: Oct. 21, 2014

(54) MATERIAL TESTING SYSTEM

(75) Inventor: Takehiko Fukuda, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 196 days.

(21) Appl. No.: 13/695,974

(22) PCT Filed: May 6, 2010

(86) PCT No.: PCT/JP2010/057755
§ 371 (c)(1),
(2), (4) Date: Nov. 2, 2012

(87) PCT Pub. No.: WO2011/138825
PCT Pub. Date: Nov. 10, 2011

(65) Prior Publication Data
US 2013/0042696 A1 Feb. 21, 2013

(51) Int. Cl.
*G01L 1/24* (2006.01)
*G01N 3/04* (2006.01)
*G01N 3/06* (2006.01)

(52) U.S. Cl.
CPC .......... *G01N 3/04* (2013.01); *G01N 2203/0405* (2013.01); *G01N 2203/0647* (2013.01); *G01N 3/068* (2013.01)
USPC ........................................................ 73/800

(58) Field of Classification Search
USPC ........................................................ 73/800
See application file for complete search history.

(56) References Cited

U.S. PATENT DOCUMENTS

| | | | | |
|---|---|---|---|---|
| 4,987,412 A | * | 1/1991 | Vaitekunas et al. | ........... 345/635 |
| 5,178,017 A | * | 1/1993 | Dinzburg | ........... 73/849 |
| 6,718,833 B2 | * | 4/2004 | Xie et al. | ........... 73/812 |
| 6,721,667 B2 | * | 4/2004 | Banes et al. | ........... 702/41 |

FOREIGN PATENT DOCUMENTS

| | | |
|---|---|---|
| JP | 06-167433 A | 6/1994 |
| JP | 2002-365188 A | 12/2002 |
| JP | 2004-257925 A | 9/2004 |
| JP | 2005-003577 A | 1/2005 |

OTHER PUBLICATIONS

International Search Report of PCT/JP2010/057755, mailing date Jun. 15, 2010.

* cited by examiner

*Primary Examiner* — Lisa Caputo
*Assistant Examiner* — Octavia Hollington
(74) *Attorney, Agent, or Firm* — Westerman, Hattori, Daniels & Adrian, LLP

(57) ABSTRACT

Provided is a material testing system provided with: an upper gripper 21 and a lower gripper 22 that grip a test piece 10; a video camera 18 that photographs the upper gripper 21 and the lower gripper 22 and the test piece 10; a first display part 25; a second display part 26; and a setting support section 61 that, in order to do test preparation where the test piece 10 is made to be gripped by the upper gripper 21 and the lower gripper 22, on the second display part 26, together with an image around the upper gripper 21 and the lower gripper 22, displays setting position indicators that support at least any one of positioning of the grippers, attachment of the test piece, and placement of gage marks to be marked on the test piece that is in a state of being gripped by the grippers.

9 Claims, 7 Drawing Sheets

MATERIAL TESTING SYSTEM

TECHNICAL FIELD

The present invention relates to a material testing system that applies test force to a test piece to perform material testing.

BACKGROUND ART

Such a material testing system has a configuration in which, for example, a pair of screw rods is supported on a table rotatably in synchronization with each other, and both end parts of a crosshead are supported by the screw rods through nuts. Also, by using rotation of a motor to rotate the pair of screw rods in synchronization with each other, the crosshead is moved along the pair of screw rods. The crosshead and the table are respectively connected with grippers. The material testing system is configured to, in a state where both ends of a test piece are gripped by the pair of grippers, move the crosshead to thereby apply test force to the test piece.

In such a material testing system, the test force acting on the test piece is detected by a load cell or the like. Also, a displacement in distance between gage marks on the test piece is measured by a displacement measuring part. Data on the displacement measured by the displacement measuring part is sampled by a sampling part, and the displacement data on the test piece is taken in together with piece of data on the test force acting on the test piece, and the like.

As the displacement measuring part, a part provided with: a video camera that photographs an image of a test piece; and an image processing circuit that, from the image of the test piece photographed by the video camera, extracts a displacement of the test piece, and outputs a measurement result of the displacement of the test piece is also used (see, for example, Patent literature 1).

A material testing system described in Patent literature 1 performs image processing of an output from the video camera provided so as to bring grippers into view, and thereby recognizes a shape of the grippers. The material testing system is also configured to move a crosshead so as to meet a distance between the grippers, which is set on the basis of information read on the basis of the shape recognition of the grippers. This eliminates the need for positioning of the grippers by manual operation in the material testing system.

Further, there is also known a material testing system in which, when an operator attaches a test piece to grippers, an auxiliary indication indicating whether the center of the test piece is aligned with a load axis of the pair of grippers is displayed, and thereby the operator can do work of making the grippers grip the test piece while seeing a monitor (see, for example, Patent literature 2).

CONVENTIONAL TECHNIQUE LITERATURE

Patent Literature

[Patent literature 1] JPA 2002-365188
[Patent literature 2] JPA H06-167433

SUMMARY OF THE INVENTION

Problem to be Solved by the Invention

However, even if any of the conventional material testing systems can automatically set the distance between the grippers, a check whether or not the test piece is successfully vertically attached to the grippers is simply visually made. Also, even if an operator does the work of attaching the test piece to the grippers with seeing the auxiliary indication as described in Patent literature 2, and can thereby easily check that the test piece is successfully vertically attached, the positioning of the distance between the grippers in a step previous to the checking is in a situation where the operator vertically moves a crosshead while seeing a scale held in operator's hand. As described, in any of the conventional material testing system, both of the two types of work, i.e., the positioning of the distance between the grippers and the attachment of the test piece to the grippers, cannot be efficiently and accurately done. Also, one of the positioning of the distance between the grippers and the attachment of the test piece to the grippers is visually checked by the operator, and therefore there is a problem that variations in setting occur among respective operators.

Also, in a material testing system that performs tensile testing, it is necessary to mark a marked line for measuring a distance between gage marks GL (Gage Length) on a test piece. In this case, in a conventional material testing system, in a state where grippers are made to grip the test piece, an operator marks the marked line between positions equally distant from the center in a load axis direction of the test piece while placing a scale on the test piece. For this reason, there is a problem that differences in setting among respective operators result in variations in gage length GL.

The present invention is made in order to solve the above-described problems, and intended to provide a material testing system that enables variations in setting accuracy of grippers, a test piece, and the like to be reduced, and test preparation to be efficiently and accurately done.

Means Adapted to Solve the Problem

An invention according to a first aspect of the present invention is a material testing system that applied test force to a test piece to thereby perform material testing, and the material testing system is provided with: a pair of grippers that grips the test piece; a photographing part that photographs the pair of grippers and the test piece; a first display part that displays at least one of an image of the test piece that is photographed by the photographing part and applied with the test force, a test condition, and a measured value; and setting support means adapted to, in order to do test preparation where the test piece is made to be gripped by the pair of grippers, on a second display part that is different from the first display part, together with an image around the pair of grippers, display setting position indicators that support at least any one of positioning of the pair of grippers, attachment of the test piece, and placement of gage marks to be marked on the test piece that is in a state of being gripped by the pair of grippers.

An invention according to a second aspect of the present invention is the invention according to the first aspect, wherein: the first display part is placed with being separated from a main body of the material testing system; and the second display part is placed in a vicinity of the pair of grippers in the main body of the material testing system.

An invention according to a third aspect of the present invention is the invention according to the second aspect, wherein when the test force is applied to the test piece, the second display part displays the image of the test piece that is photographed by the photographing part and applied with the test force, and the measured value.

An invention according to a fourth aspect of the present invention is the invention according to the second aspect, wherein the setting position indicators that are displayed on the second display part by the setting support means and support arrangement of the pair of grippers include a horizontal line that represents a moving position of one of the pair of grippers.

An invention according to a fifth aspect of the present invention is the invention according to the fourth aspect, wherein the setting support means changes a display position of the horizontal line depending on a type of the pair of grippers selected according to a test purpose, and a length of the test piece.

An invention according to a sixth aspect of the present invention is the invention according to the second aspect, wherein the setting position indicators that are displayed on the second display part by the setting support means and support arrangement of the test piece include a line that represents a position of at least one side end of the test piece.

An invention according to a seventh aspect of the present invention is the invention according to the sixth aspect, wherein the setting support means changes a display position of the line depending on a width of a selected test piece.

An invention according to an eighth aspect of the present invention is the invention according to the second aspect, wherein the setting position indicators that are displayed on the second display part by the setting support means and support arrangement of the gage marks to be marked on the test piece that is in the state of being gripped by the pair of grippers include lines that represent positions of the gage marks.

An invention according to a ninth aspect of the present invention is the invention according to the eighth aspect, wherein the setting support means changes display positions of the lines depending on a distance between the gage marks to be marked on the test piece that is in the state of being gripped by the pair of grippers.

Effects of the Invention

According to the inventions according to the first to ninth aspects, the material testing system is provided with the setting support means adapted to, on the second display part that is different from the first display part, together with the image around the pair of grippers, display the setting position indicators that support any of the arrangement of the pair of grippers, the arrangement of the test piece, and the arrangement of the gage marks to be marked on the test piece that is in the state of being gripped by the pair of grippers, and therefore an operator doing test preparation can do work while seeing the setting position indicators displayed on the second display part. For this reason, differences in accuracy of the arrangement of the grippers, the arrangement of the test piece, or the like can be prevented from occurring among respective operators, and therefore such arrangement can be accurately performed.

According to the invention according to the second aspect, the second display part is placed in the vicinity of the pair of grippers in the main body of the material testing system, and therefore from a position of the operator doing test preparation work, the setting position indicators can be seen on the same eye line as that for the grippers, test piece, and the like that are work objects. For this reason, the operator can more accurately perform the arrangement of the grippers, the arrangement of the test piece, or the like while seeing the setting position indicators displayed on the second display part without changing a position thereof during the test preparation work.

According to the invention according to the third aspect, when the test force is applied to the test piece, the second display part displays the image of the test piece that is photographed by the photographing part and applied with the test force, and the measured value, and therefore usability of the first display part, which is also used as a control monitor for the whole of the material testing system and a calculator monitor for data processing, during testing can be improved.

EMBODIMENTS OF THE INVENTION

Figure 1:
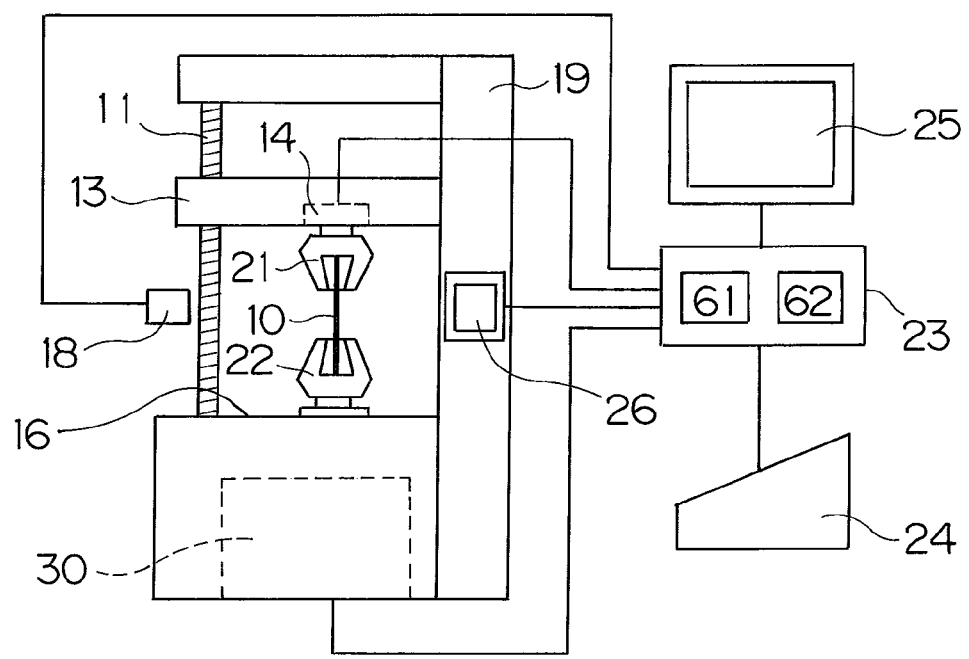
FIG. 1 is a schematic diagram of a material testing system according to the present invention.

Embodiments of the present invention will hereinafter be described on the basis of the drawings. FIG. 1 is a schematic diagram of a material testing system according to the present invention.

The material testing system is provided with: a table 16; a pair of supports 19 that is provided upright on a floor surface; a pair of screw rods 11 that is rotatably provided upright on the table 16 inside the respective supports 19 with facing in a vertical direction; a crosshead 13 that is movable along the screw rods 11; and a load mechanism 30 that is intended to move the crosshead 13 to apply test force to a test piece 10. Note that FIG. 1 illustrates a state where, of the pair of supports 19, the support 19 on the left-hand side in the diagram is removed.

The crosshead 13 is connected to the pair of screw rods 11 through unillustrated nuts. The pair of screw rods 11 is configured such that a lower end part of each of the screw rods 11 is connected to the load mechanism 30, and power from a power source of the load mechanism 30 is transferred to the pair of screw rods 11. The pair of screw rods 11 rotates in synchronization with each other, and thereby the crosshead 13 moves up and down along the pair of screw rods 11.

On the crosshead 13, an upper gripper 21 for gripping an upper end part of the test piece 10 is annexed. On the other hand, on the table 16, a lower gripper 22 for gripping a lower end part of the test piece 10 is annexed. In the case of performing tensile testing, by moving up the crosshead 13 with gripping the both end parts of the test piece 10 by the upper gripper 21 and the lower gripper 22, the test force (tensile load) is loaded on the test piece 10.

At this time, the test force acting on the test piece 10 is detected by a load cell 14, and then inputted to a control part 23. Also, the test piece 10 is photographed by a video camera 18, and an image of the test piece 10 is inputted to the control part 23. Note that the video camera 18 is positioned so as to bring the upper gripper 21 and the lower gripper 22 into one view.

The control part 23 is provided with a setting support section 61, and configured to have: a storage section 62 such as a ROM or RAM; and a computer or sequencer provided with a CPU and the like. The control part 23 is connected with: a first display part 25 and a second display part 26 that are respectively display devices such as liquid crystal displays; an input part 24 that has a mouse, keyboard, and the like; the load cell 14; the video camera 18; and the load mechanism 30. Also, the control part 23 takes in test force data from the load cell 14 and photographed image data from the video camera 18 to perform data processing. By performing such processing such as calculation in the control part 23, a displacement in distance between gage marks on the test piece 10 is obtained.

The setting support section 61 functions as setting support means adapted to, in the material testing system, in order to do test preparation where the upper gripper 21 and the lower gripper 22 are made to grip the test piece 10, perform: a gripper setting support function that supports positioning of the upper gripper 21 and the lower gripper 22; a test piece setting support function that supports attachment of the test piece 10; and a gage mark setting support function that supports placement of the gage marks to be marked on the test piece that is in the state of being gripped by the upper gripper 21 and the lower gripper 22.

In the material testing system, the first display part 25 is placed with being separated from a main body of the material testing system together with the control part 23 and input part 24. During testing, the first display part 25 displays at least one of an image of the test piece that is photographed by the photographing part and applied with the test force, test conditions, and a measured value, and functions as a control monitor for the whole of the material testing system and a calculator monitor for data processing.

On the other hand, the second display part 26 is placed in the vicinity of the upper gripper 21 and the lower gripper 22 in front of the supports 19. The vicinity of the upper gripper 21 and the lower gripper 22 refers to a position that is near a space placed between the pair of supports 19, where setting work such as the positioning of the upper gripper 21 and the lower gripper 22 is done in order to do the test preparation, and at almost the same height as that of eyes of an operator at the time doing such work.

Next, operation in the material testing system at the time of doing the test preparation prior to material testing that applies the test force to the test piece 10 is described. In the case of doing the test preparation in the material testing system, the gripper setting support function, test piece setting support function, and gage mark setting support function are performed in this order.

Figure 2:
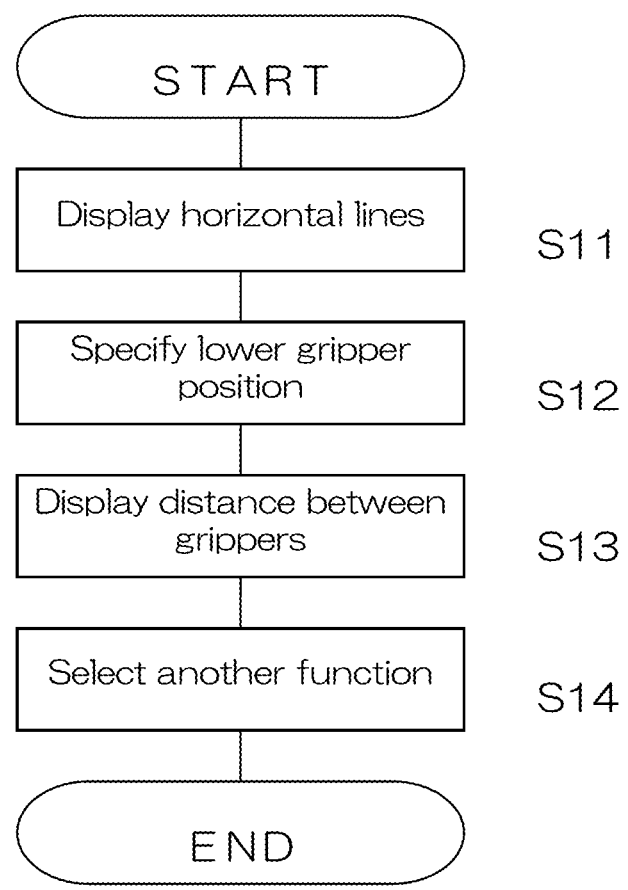
FIG. 2 is a flowchart illustrating operation of a gripper setting support function.
Figure 3:
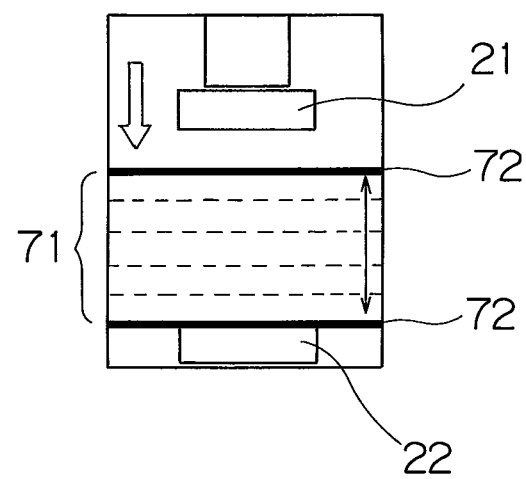
FIG. 3 is a schematic diagram illustrating a display screen of a second display part 26.

First, operation performed by the setting support section 61 in order to do the test preparation where the upper gripper 21 and the lower gripper 22 are made to grip the test piece 10 is described. FIG. 2 is a flowchart illustrating the operation of the gripper setting support function, and FIG. 3 is a schematic diagram illustrating a display screen of the second display part 26 in this case.

When the gripper setting support function is selected on the basis of input from the input part 24, by action of the setting support section 61 of the control part 23, a plurality of horizontal lines 71 are displayed at regular intervals so as to be superimposed on a live image around the upper gripper 21 and the lower gripper 22 that are preliminarily displayed on the second display part 26 (Step S11). These horizontal lines 71 are lines orthogonal to a load axis of the testing.

Then, on the basis of input from the input part 24 by an operator, a fore end position of the lower gripper 22 is specified (Step S12). By doing so, as indicated by thick lines in FIG. 3, two horizontal lines 72 representing a distance between the grippers are displayed on the second display part 26 (Step S13). Of the two horizontal lines 72 indicated by the thick lines in FIG. 3, a lower line is a line that coincides with the fore end position of the lower gripper 22, which is specified in Step S12, and an upper line represents a moving position to which the upper gripper 21 is to be moved. The display of the horizontal lines 71 and 72 on the second display part 26 is changed depending on the type of the pair of grippers selected according to a test purpose and a length of the test piece. That is, the display of the lines on the second display part 26 is provided by calling up display data that is preliminarily stored in the storage section 62 with being related to the type of the grippers selected according to the test purpose, the length of the test piece 10, and the like, and represents the distance between the upper gripper 21 and the lower gripper 22. Accordingly, the two horizontal lines 72 indicated by the thick lines in FIG. 3 represent the distance between the upper gripper 21 and the lower gripper 22 in such test conditions. In addition, the plurality of horizontal lines 71 displayed on the second display part 26 in Step S11 remains displayed on the second display part 26 as auxiliary lines.

The operator moves the upper gripper 21 by manual operation with targeting the horizontal line 72 that is displayed on the second display part 26 and corresponds to the moving position of the upper gripper 21. After that, when the operator selects another function or other operation such as the test piece setting support (Step S14), a series of operation of the gripper setting support function ends. Note that even if the operator does not select another function but reselects the gripper setting support function, the series of operation of the gripper setting support function ends.

Figure 4:
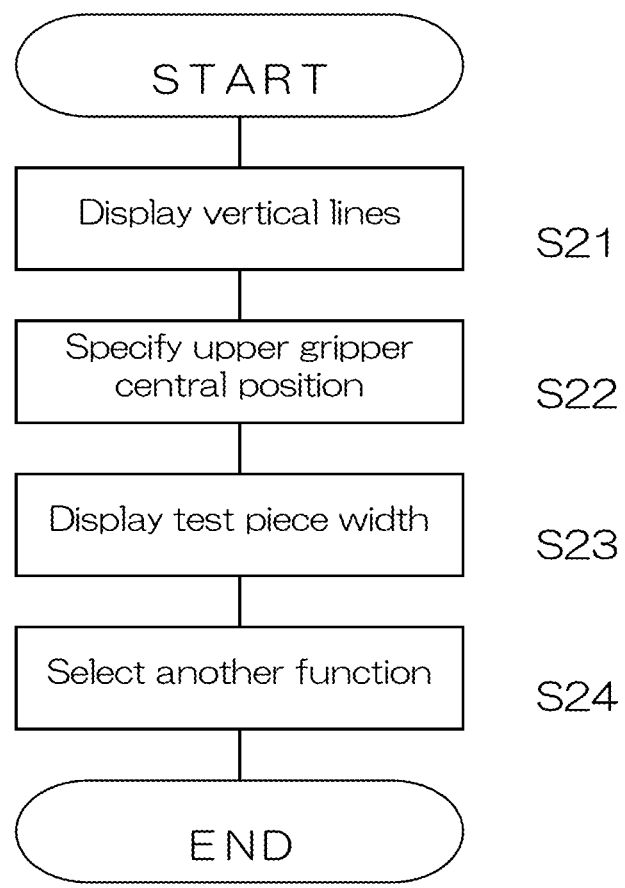
FIG. 4 is a flowchart illustrating operation of a test piece setting support function.
Figure 5:
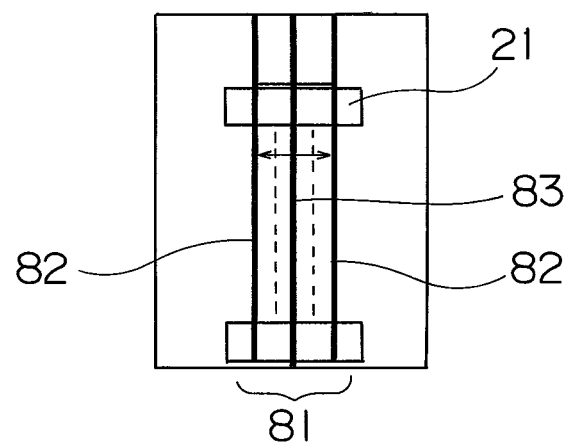
FIG. 5 is a schematic diagram illustrating a display screen of the second display part 26.

When the positioning of the gripper is completed according to the above-described procedure, the operator then attaches the test piece 10 to the upper gripper 21 and the lower gripper 22. The attachment work is done by using the test piece setting support function. FIG. 4 is a flowchart illustrating operation of the test piece setting support function, and FIG. 5 is a schematic diagram illustrating a display screen of the second display part 26 in this case.

When the test piece setting support function is selected on the basis of input from the input part 24, a plurality of vertical lines 81 parallel to the load axis of the testing are displayed around the load axis so as to be superimposed on a live image around the upper gripper 21 and the lower gripper 22 that are preliminarily displayed on the second display part 26 (Step S21).

Then, on the basis of input from the input part 24 by the operator, a central position of the upper gripper 21 in the vertical direction is specified (Step S22). By doing so, as indicated by thick lines in FIG. 5, two vertical lines 82 representing a width of the test piece and a vertical line 83 corresponding to a central axis of the test piece are displayed on the second display part 26 (Step S23). The display of the vertical lines 81, 82, and 83 on the second display part 26 is changed depending on the width of the test piece 10. That is, the display of the lines on the second display part 26 is provided by calling up display data that is preliminarily stored in the storage section 62 with being related to the width of the test piece 10, and represents positions of side ends of the test piece 10 at the time when the central axis of the test piece 10 coincides with the load axis. Accordingly, the two vertical lines 82 indicated by the thick lines in FIG. 5 represent the positions of the both side ends of the test piece 10 in this test condition. In addition, the plurality of vertical lines 81 displayed on the second display part 26 in Step S21 remains displayed on the second display part 26 as auxiliary lines.

The operator attaches the test piece 10 to the upper gripper 21 and the lower gripper 22 so as to make the central axis of the test piece 10 coincide with the load axis of the testing with targeting the vertical lines 82 that are displayed on the second display part and represent the positions of the both side ends of the test piece 10. After that, when the operator selects another function or other operation such as the gage mark setting support (Step S24), a series of operation of the test piece setting support function ends. Note that even if the operator does not select another function but reselects the test piece setting support function, the series of operation of the test piece setting support function ends.

Note that, in the present embodiment, the video camera 18 is set so as to bring the upper gripper 21 and the lower gripper 22 and the whole of the test piece 10 into one view of the second display part 26, and therefore as illustrated in FIG. 5, on the display screen, the two vertical lines 82 made to coincide with the both side ends of the test piece 10 are displayed as the thick lines. However, even in the case where the video camera 18 is set so as not to bring the whole of the test piece 10 into view, if one of the side ends of the test piece 10 is within the view, the test piece 10 can be correctly set. That is, in this case, one vertical line representing a position of one of the side ends of the test piece 10 is displayed on the second display part 26. This enables the operator to correctly attach the test piece 10 with targeting the one vertical line representing the position of the one side end of the test piece 10.

Figure 6:
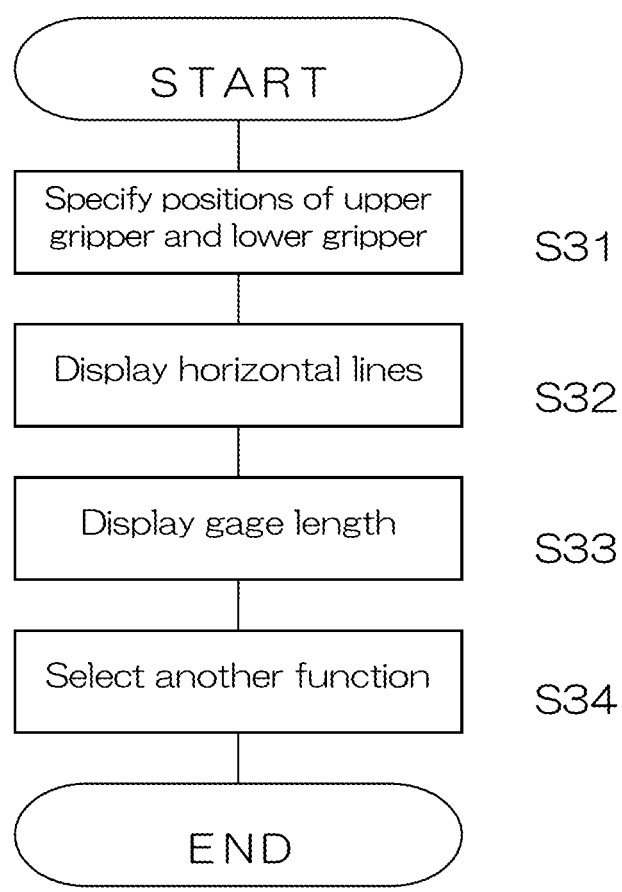
FIG. 6 is a flowchart illustrating operation of a gage mark setting support function.

When the attachment of the test piece 10 to the upper gripper 21 and the lower gripper 22 is completed according to the above-described procedure, the operator then puts gage marks on the test piece 10. The marking work is done by using the gage mark setting support function. FIG. 6 is a flowchart illustrating operation of the gage mark setting support function, and FIG. 7 is a schematic diagram illustrating a display screen of the second display part 26 in this case.

When the gage mark setting support function is selected on the basis of input from the input part 24, the operator specifies a lower end position 93 of the upper gripper 21 and an upper end position 94 of the lower gripper 22 in a live image around the upper gripper 21 and the lower gripper 22 that are displayed on the second display part 26 (Step S31). Then, a plurality of horizontal lines 91 are displayed between the upper gripper 21 and the lower gripper 22 at regular intervals so as to be superimposed on the live image around the upper gripper 21 and the lower gripper 22 (Step S32).

Figure 7:
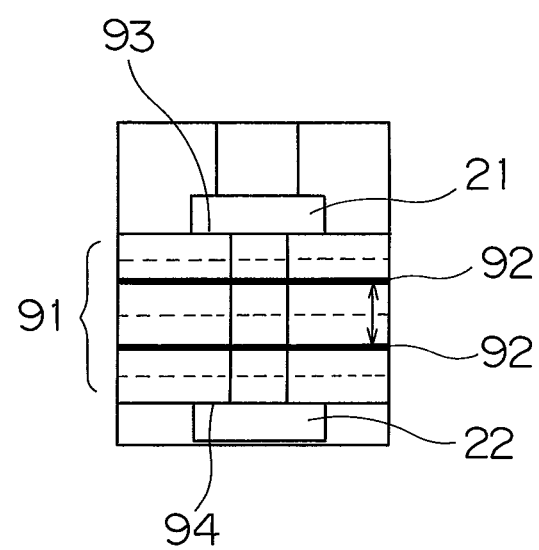
FIG. 7 is a schematic diagram illustrating a display screen of the second display part 26.

After that, as indicated by thick lines in FIG. 7, on the second display part 26, two horizontal lines 92 that are separated by a distance corresponding to a gage length GL (or a distance between the gage marks) are displayed (Step S33). The display of the horizontal lines 91 and 92 on the second display part 26 is changed depending on the gage length GL. That is, the display of the lines on the second display part 26 is provided by calling up display data, which is preliminarily stored in the storage section 62 with being related to the gage length GL and represents the gage mark positions, with using the center (intermediate point between an upper end of the upper gripper 21 and a lower end of the lower gripper 22) of the test piece 10 in a gripped state, which is obtained from the lower end position 93 of the upper gripper 21 and the upper end position 94 of the lower gripper 22 specified in Step S31, as a reference position. Accordingly, the two horizontal lines 92 indicated by the thick lines in FIG. 7 are displayed in positions separated from the center of the test piece 10 by the same distance, and represent the positions at which the gage marks are to be marked on the test piece 10 in this test condition. In addition, the plurality of horizontal lines 91 displayed on the second display part 26 in Step S32 remains displayed on the second display part 26 as auxiliary lines.

The operator attaches gage mark seals to the test piece 10 with targeting the horizontal lines 92 that are displayed on the second display part 26 and represent the gage mark positions, and can thereby place the gage marks at the correct positions. After that, when the operator selects another function or other operation (Step S34), a series of operation of the gage mark setting support function ends. Note that even if the operator does not select another function but reselects the gage mark setting support function, the series of operation of the gage mark setting support function ends.

Note that, in the present embodiment, to mark the gage marks on the test piece 10, the gage mark seals are used; however, the operator may use a marker or the like to enter the gage marks on the test piece 10 along the horizontal lines 92 representing the gage mark positions.

Also, in the present embodiment, the gage mark seals are attached with the test piece 10 being gripped by the upper gripper 21 and the lower gripper 22; however, the test piece 10 on which the gage marks are preliminarily put can also be made to be gripped by the upper gripper and the lower gripper. In this case, it is only necessary to display grid-like auxiliary lines on the display screen of the second display part 26 as well as simultaneously displaying the vertical lines 82 representing the width of the test piece and the horizontal lines 92 representing the gage length GL, and perform the test piece setting support function and the gage mark setting support function in parallel.

In the above-described embodiment, setting position indicators that support any of the positioning of the pair of grippers, the attachment of the test piece, and the placement of the gage marks to be marked on the test piece that is in the state of being gripped by the pair of grippers are represented by lines; however, various types of symbols such as arrows can be employed as the indicators if the symbols can accurately represent positions.

Also, in the above-described embodiment, the second display part 26 is set in the main body of the material testing system; however, a position of the setting does not necessarily have to be fixed. That is, various types of variations that enable the second display part 26 to be moved to a position that can be easily seen by an operator can be made.

EXPLANATIONS OF LETTERS OR NUMERALS

10: Test piece
11: Screw rod
13: Crosshead
14: Load cell
18: Video camera
19: Support
21: Upper gripper
22: Lower gripper
23: Control part
24: Input part
25: First display part
26: Second display part
30: Load mechanism
61: Setting support section
62: Storage section
72: Horizontal line
82: Vertical line
92: Horizontal line

What is claimed is:

1. A material testing system that applied test force to a test piece to thereby perform material testing, the material testing system comprising:
   a pair of grippers that grips the test piece;
   a photographing part that photographs the pair of grippers and the test piece;
   a first display part that displays at least one of an image of the test piece that is photographed by the photographing part and applied with the test force, a test condition, and a measured value; and
   setting support means adapted to, in order to do test preparation where the test piece is made to be gripped by the pair of grippers, on a second display part that is different from the first display part, together with an image around the pair of grippers, display setting position indicators that support at least any one of positioning of the pair of grippers, attachment of the test piece, and placement of gage marks to be marked on the test piece that is in a state of being gripped by the pair of grippers.

2. The material testing system according to claim 1, wherein:
   the first display part is placed with being separated from a main body of the material testing system; and
   the second display part is placed in a vicinity of the pair of grippers in the main body of the material testing system.

3. The material testing system according to claim 2, wherein
   when the test force is applied to the test piece, the second display part displays the image of the test piece that is photographed by the photographing part and applied with the test force, and the measured value.

4. The material testing system according to claim 2, wherein
   the setting position indicators that are displayed on the second display part by the setting support means and support arrangement of the pair of grippers include a horizontal line that represents a moving position of one of the pair of grippers.

5. The material testing system according to claim 4, wherein
   the setting support means changes a display position of the horizontal line depending on a type of the pair of grippers selected according to a test purpose, and a length of the test piece.

6. The material testing system according to claim 2, wherein
   the setting position indicators that are displayed on the second display part by the setting support means and support arrangement of the test piece include a line that represents a position of at least one side end of the test piece.

7. The material testing system according to claim 6, wherein
   the setting support means changes a display position of the line depending on a width of a selected test piece.

8. The material testing system according to claim 2, wherein
   the setting position indicators that are displayed on the second display part by the setting support means and support arrangement of the gage marks to be marked on the test piece that is in the state of being gripped by the pair of grippers include lines that represent positions of the gage marks.

9. The material testing system according to claim 8, wherein
   the setting support means changes display positions of the lines depending on a distance between the gage marks to be marked on the test piece that is in the state of being gripped by the pair of grippers.

* * * * *